United States Patent
Ventura et al.

(10) Patent No.: US 10,927,006 B2
(45) Date of Patent: Feb. 23, 2021

(54) THIN FILM SUBSTRATES INCLUDING CROSSLINKED CARBON NANOSTRUCTURES AND RELATED METHODS

(71) Applicant: Baker Hughes Holdings LLC, Houston, TX (US)

(72) Inventors: Darryl N. Ventura, Houston, TX (US); Rostyslav Dolog, Houston, TX (US); Sankaran Murugesan, Katy, TX (US); Radhika Suresh, Sugar Land, TX (US); Valery N. Khabashesku, Houston, TX (US); Qusai Darugar, Houston, TX (US)

(73) Assignee: Baker Hughes Holdings LLC, Houston, TX (US)

( * ) Notice: Subject to any disclaimer, the term of this patent is extended or adjusted under 35 U.S.C. 154(b) by 227 days.

(21) Appl. No.: 15/868,129

(22) Filed: Jan. 11, 2018

(65) Prior Publication Data

US 2018/0194620 A1 Jul. 12, 2018

Related U.S. Application Data

(60) Provisional application No. 62/444,872, filed on Jan. 11, 2017.

(51) Int. Cl.
*C01B 32/174* (2017.01)
*B82B 3/00* (2006.01)
(Continued)

(52) U.S. Cl.
CPC .......... *B82B 3/0038* (2013.01); *C01B 32/174* (2017.08); *C01B 32/194* (2017.08);
(Continued)

(58) Field of Classification Search
CPC ....... B82Y 30/00; B82Y 40/00; B82B 1/0038; G01N 21/658; G01N 33/54373; C01B 32/174; C01B 32/194
See application file for complete search history.

(56) References Cited

U.S. PATENT DOCUMENTS

| 6,031,711 A | 2/2000 | Tennent et al. |
| 6,099,965 A | 8/2000 | Tennent et al. |

(Continued)

FOREIGN PATENT DOCUMENTS

| KR | 101589039 B1 | 1/2016 |
| WO | WO-2015145155 A1 * | 10/2015 |

OTHER PUBLICATIONS

Afrin, R., and N. A. Shah. "Room temperature gas sensors based on carboxyl and thiol functionalized carbon nanotubes buckypapers." Diamond and Related Materials 60 (2015): 42-49.*

(Continued)

*Primary Examiner* — Richard M Rump
(74) *Attorney, Agent, or Firm* — TraskBritt

(57) ABSTRACT

A method of making a thin film substrate involves exposing carbon nanostructures to a crosslinker to crosslink the carbon nanostructures. The crosslinked carbon nanostructures are recovered and disposed on a support substrate. A thin film substrate includes crosslinked carbon nanostructures on a support substrate. The crosslinked carbon nanostructures have a crosslinker between the carbon nanostructures. A method of performing surface enhanced Raman spectroscopy (SERS) on a SERS-active analyte involves providing a SERS-active analyte on such a thin film substrate, exposing the thin film substrate to Raman scattering, and detecting the SERS-active analyte.

4 Claims, 4 Drawing Sheets

(51) Int. Cl.
*C01B 32/194* (2017.01)
*G01N 33/543* (2006.01)
*G01N 21/65* (2006.01)
*B82Y 40/00* (2011.01)
*B82Y 30/00* (2011.01)

(52) U.S. Cl.
CPC ..... *G01N 21/658* (2013.01); *G01N 33/54373* (2013.01); *B82Y 30/00* (2013.01); *B82Y 40/00* (2013.01)

(56) References Cited

U.S. PATENT DOCUMENTS

| | | | |
|---|---|---|---|
| 6,746,627 B2 | 6/2004 | Niu et al. | |
| 6,872,681 B2 | 3/2005 | Niu et al. | |
| 7,081,429 B2* | 7/2006 | Kishi | B01J 21/18 423/447.1 |
| 7,341,498 B2 | 3/2008 | Takai et al. | |
| 7,623,340 B1 | 11/2009 | Song et al. | |
| 8,057,901 B2 | 11/2011 | Ford et al. | |
| 8,665,581 B2 | 3/2014 | Fleischer et al. | |
| 8,976,507 B2 | 3/2015 | Aria et al. | |
| 2009/0088582 A1* | 4/2009 | Inagaki | B82Y 40/00 556/143 |
| 2009/0166560 A1 | 7/2009 | Dai et al. | |
| 2011/0189452 A1* | 8/2011 | Lettow | B05D 3/10 428/220 |
| 2012/0164433 A1 | 6/2012 | Advincula | |
| 2014/0138587 A1 | 5/2014 | Pasquali et al. | |
| 2017/0106342 A1* | 4/2017 | Raveendran-Nair | G01N 15/082 |

OTHER PUBLICATIONS

Park, Sungjin, et al. "Graphene oxide papers modified by divalent ions—enhancing mechanical properties via chemical cross-linking." ACS nano 2.3 (2008): 572-578.*

Kwon, Ki Young, et al. "High-performance biosensors based on enzyme precipitate coating in gold nanoparticle-conjugated single-walled carbon nanotube network films." Carbon 48.15 (2010): 4504-4509.*

Ventura, Darryl N. Synthesis of cross-linked carbon nanotube mats and their applications. The Florida State University, 2011.*

Ventura, Darryl N., et al. "Assembly of cross-linked multi-walled carbon nanotube mats." Carbon 48.4 (2010): 987-994.*

Ventura, Darryl N., et al. "A flexible cross-linked multi-walled carbon nanotube paper for sensing hydrogen." Carbon 50.7 (2012): 2672-2674.*

Duan, Jingjing, et al. "Porous C3N4 nanolayers@ N-graphene films as catalyst electrodes for highly efficient hydrogen evolution." ACS nano 9.1 (2015): 931-940.*

Zhang, Jianwei, et al. "Enhanced mechanical and electrical properties of carbon nanotube buckypaper by in situ cross-linking." Carbon 63 (2013): 125-132.*

Wan, Sijie, et al. "Bioinspired graphene-based nanocomposites and their application in flexible energy devices." Advanced Materials 28.36 (2016): 7862-7898.*

Ou, Xiaowei, et al. "Highly Stable Graphene-Based Multilayer Films Immobilized via Covalent Bonds and Their Applications in Organic Field-Effect Transistors." Advanced Functional Materials 23.19 (2013): 2422-2435.*

International Search Report for International Application No. PCT/US2018/013300 dated May 2, 2018, 4 pages.

International Written Opinion for International Application No. PCT/US2018/013300 dated May 2, 2018, 6 pages.

Patel et al., Fabrication and Cytocompatibility of In Situ Cross-linked Carbon Nanomaterial Films, Scientific Reports, vol. 5, Article No. 10261, (2015), 37 pages.

Sun et al., Highly Sensitive Surface-Enhanced Raman Scattering Substrate Made from Superaligned Carbon Nanotubes, Nano Lett., vol. 10, No. 5, (2010), pp. 1747-1753 (abstract only).

Poshkus, Algirdas C., Improved Synthesis of Basic Zinc Acetate, Hexakis (u-acetato)-u-oxatetrazinc, Ind. Eng. Chem. Prod. Res. Dev., vol. 22, No. 2, (1983), pp. 380-381.

Gao et al, Direct Intertube Cross-Linking of Carbon Nanotubes at Room Temperature, American Chemical Society, Nano Letters, vol. 16, No. 10, (2016), 6541-6547.

Ventura et al., Assembly of Cross-Linked Multi-Walled Carbon Nanotube Mats, Carbon, vol. 48, (2010), pp. 987-994.

Russian Office Action for Russian Application No. 2019125175, dated May 18, 2020, 5 pages.

* cited by examiner

THIN FILM SUBSTRATES INCLUDING CROSSLINKED CARBON NANOSTRUCTURES AND RELATED METHODS

CROSS-REFERENCE TO RELATED APPLICATION

This application claims the benefit under 35 U.S.C. § 119(e) of U.S. Provisional Patent Application Ser. No. 62/444,872, filed Jan. 11, 2017, the disclosure of which is hereby incorporated herein in its entirety by this reference.

TECHNICAL FIELD

Embodiments of the disclosure relate generally to thin film substrates for use in Surface Enhanced Raman Spectroscopy (SERS), filtration, and chemical sensing, and to methods of making and using the thin film substrates. More particularly, embodiments of the disclosure relate to thin film substrates including crosslinked carbon nanostructures and to methods of making and using the thin film substrates.

BACKGROUND

Surface Enhanced Raman Spectroscopy (SERS) is an analytical technique used to detect a SERS-active analyte, such as a biological molecule. In SERS, a liquid sample to be analyzed is placed on a SERS substrate and up to a single molecule of the analyte is detectable. Conventional SERS substrates include metallic nanoparticles on a solid support, such as borosilicate glass or mica. The SERS substrate may also be a carbon nanotube (CNT) mat, which is conventionally formed using mechanical compression, physical compression, or destructive electron beam irradiation techniques. Since these techniques use compression or laser ablation, the techniques may be destructive to the SERS substrate. The mechanical compression of CNTs into mats relies on weak van der Waals interactions between the CNTs, while the laser ablation requires high energy electron beams to fuse the CNTs together, which often results in excessive destruction of the $sp^2$ bonding and can adversely affect CNT properties. Due to the weak van der Waals interactions between the CNTs, mechanically compressed CNTs may absorb liquid and swell when exposed to liquid samples. Moreover, conventional methods are not industrially viable as they often utilize specialized equipment, such as high energy lasers or high pressure/high temperature (HPHT) reaction chambers.

BRIEF SUMMARY

Embodiments disclosed herein include methods of making a thin film substrate. The method comprises exposing carbon nanostructures to a crosslinker to crosslink the carbon nanostructures. The crosslinked carbon nanostructures are recovered and disposed on a support substrate.

In additional embodiments, thin film substrates are disclosed. The thin film substrate comprises crosslinked carbon nanostructures on a support substrate. The crosslinked carbon nanostructures comprise a crosslinker between the carbon nanostructures.

In yet additional embodiments, methods of performing surface enhanced Raman spectroscopy (SERS) to detect a SERS-active analyte are disclosed. The method comprises providing a SERS-active analyte on a thin film substrate, exposing the thin film substrate to Raman scattering, and detecting the SERS-active analyte. The thin film substrate comprises crosslinked carbon nanostructures on a support substrate and the crosslinked carbon nanostructures comprise a crosslinker between the carbon nanostructures.

DETAILED DESCRIPTION

Illustrations presented herein are not meant to be actual views of any particular material or component, but are merely idealized representations that are employed to describe embodiments of the disclosure.

The following description provides specific details, such as material types, compositions, material thicknesses, and processing conditions in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional techniques employed in the industry. In addition, the description provided below does not form a complete process flow for forming a thin film substrate. Only those process acts and structures necessary to understand the embodiments of the disclosure are described in detail below. Additional acts or materials to form the thin film substrates may be performed by conventional techniques.

Figure 1:
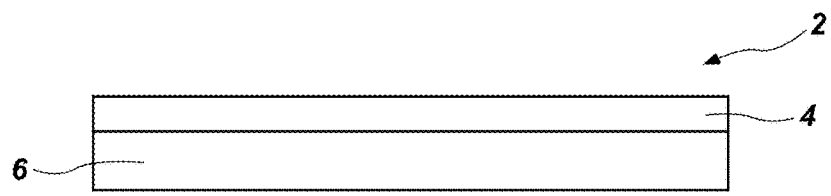
FIG. 1 is a schematic diagram of a thin film substrate including the crosslinked carbon nanotubes on a support substrate according to an embodiment of the disclosure.

A thin film substrate 2 is formed from and includes crosslinked carbon nanostructures 4 on a support substrate 6, as shown in FIG. 1. The thin film substrate 2 may be used for Surface Enhanced Raman Spectroscopy (SERS), filtration, or chemical sensing. The carbon nanostructures may be exposed to a crosslinker, such as in solution, to crosslink the carbon nanostructures. As described in more detail below, the carbon nanostructures and crosslinker may be combined in an appropriate solvent, such as water, an organic solvent, or combinations thereof. The crosslinked carbon nanostructures 4 may be configured as carbon nanostructure mats or in other configurations. As used herein, the term "carbon nanostructure mat" means and includes a sheet of carbon nanostructures. The carbon nanostructure mat may include a plurality of randomly oriented carbon nanostructures. The carbon nanostructure mats may have a thickness of between, for example, about 100 μm and about 500 μm, such as between about 100 μm and about 400 μm, or between about 200 μm and about 300 μm. The thin film substrates 2 including the crosslinked carbon nanostructures 4 may be formed by combining components in solution and recovering the crosslinked carbon nanostructures 4 by simple filtration-from-suspension techniques. A suspension containing the crosslinked carbon nanostructures 4 may be filtered, such as by vacuum filtration, to recover the crosslinked carbon nanostructures 4. The crosslinked carbon nanostructures 4 may, optionally, be disposed on or applied to the support substrate 6. The support substrate 6 may be a solid support or a flexible, free standing support. However, the crosslinked carbon nanostructures 4 may be of sufficient strength that a support substrate 6 is not utilized. The crosslinked carbon nanostructures 4 may exhibit sufficient mechanical integrity that the crosslinked carbon nanostructures 4 may be used free-standing, without a support substrate 6. The crosslinked carbon nanostructures 4 without the support substrate 6 may also be configured as carbon nanostructure mats or in other configurations. Thus, industrially viable quantities of the crosslinked carbon nanostructures 4 may be easily formed. Crosslinking of the carbon nanostructures may be conducted using multivalent cations, pi-pi stacking, covalent bonding, or electrostatic interactions. The crosslinker may be an atomic element, a chemical compound, a functional group, or a bond between the carbon nanostructures. The resulting thin film substrates 2 including the crosslinked carbon nanostructures 4 may be flexible and exhibit good mechanical properties for use in SERS, such as in detecting a SERS-active analyte. Optionally, nanowires formed of platinum, copper, silver, gold, ruthenium, rhodium, tin, palladium, aluminum, lithium, sodium, potassium, or combinations thereof may be present in the thin film substrates 2 to synergistically increase detection of the SERS-active analyte (e.g., enhance the detected Raman signal of the SERS-active analyte). The resulting thin film substrates 2 including the crosslinked carbon nanostructures 4 may also be used in filtration and chemical sensing.

The crosslinker may be used to crosslink the carbon nanostructures and form the crosslinked carbon nanostructures 4. As explained in more detail below, the crosslinker may be a cation source compound, a pi-orbital source compound, a crosslinking agent, or metal nanoparticles. Nanoparticles of the crosslinker may be used, such as having an average particle size of from greater than or equal to about 1 nm to less than or equal to about 50 nm, from greater than or equal to about 1 nm to less than or equal to about 20 nm, or from greater than or equal to about 1 nm to less than or equal to about 10 nm. The carbon nanostructures may have a larger relative particle size than the particle size of the crosslinker, enabling formation of a small amount of the crosslinker between the carbon nanostructures. The crosslinker may be commercially available, or may be produced by conventional techniques.

The carbon nanostructures may include an sp2 carbon structure, such as graphene or CNTs. The CNTs may be single-walled carbon nanotubes (SWCNTs), double-walled carbon nanotubes (DWCNTs), multi-walled carbon nanotubes (MWCNTs), or a combination thereof. In some embodiments, the carbon nanostructures are multi-walled carbon nanotubes. The carbon nanostructures may be functionalized, such as with one or more functional groups formulated and configured to bond, react, or otherwise interact with the crosslinker or with other carbon nanostructures. By way of nonlimiting example, the functional groups include amine groups, carboxyl groups (—COOH), thiol groups, fluorine or fluorinated functional groups, hydroxyl groups, or combinations thereof. The carbon nanostructures, such as the CNTs, may be commercially available, such as from Nanocyl SA (Sambreville, Belgium) or MER Corporation (Tucson, Ariz.), or may be produced by conventional techniques. Commercially available carbon nanostructures may be used in their as-received form or may be functionalized, such as with carboxylate or other functional groups. Carboxylated carbon nanostructures, such as carboxylated CNTs, may be produced, for example, by reacting the CNTs with at least one of nitric acid and sulfuric acid. Alternatively, the functionalized carbon nanostructures may be commercially available and used in their as-received form.

Figure 2:
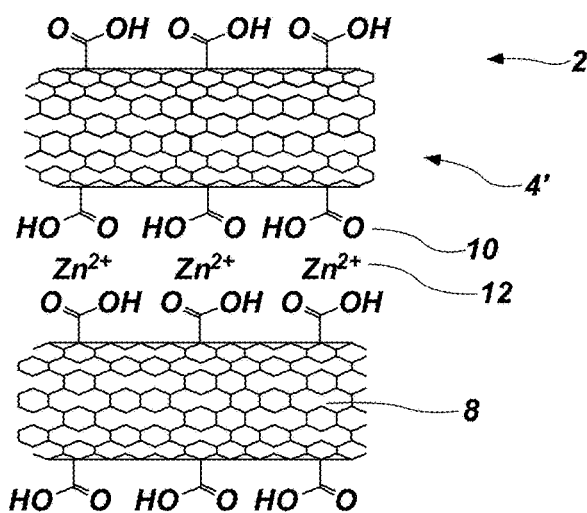
FIG. 2 is a schematic diagram of a thin film substrate including crosslinked carbon nanotubes according to an embodiment of the disclosure.

In one embodiment, the thin film substrate 2 includes CNTs 8 crosslinked by the multivalent cations 12, as shown in FIG. 2. However, the thin film substrate 2 may, alternatively, include other carbon nanostructures crosslinked by the multivalent cations 12. The multivalent cation 12 may be obtained from a multivalent cation source compound. As used herein, the term "multivalent cation source compound" means and includes a chemical compound that includes a multivalent cation and a corresponding anion. The multivalent cation 12 is formulated to react and crosslink with the CNTs 8. The thin film substrate 2 may be formed by crosslinking the CNTs 8 with the cation source compound. The CNTs 8 are functionalized with a functional group 10 that is reactive with the multivalent cation 12 of the cation source compound. The functional groups 10 on the CNTs 8 may be formulated to react with the multivalent cation 12 by an ion exchange reaction. The multivalent cation 12 may be a divalent ($2^+$) or higher cation, such as zinc, magnesium, calcium, aluminum, titanium, zirconium, niobium, or combinations thereof. The multivalent cation source compound may be a metal oxide, e.g., zinc oxide, MgO, CaO, $Al_2O_3$, a metal alkoxide, e.g., titanium isopropoxide, titanium ethoxide, zirconium ethoxide, aluminum isopropoxide, niobium ethoxide, or other oxide, salt, or complex of the multivalent cation, or combinations thereof. The multivalent cation source compound may also be an acetate of the multivalent cation, ammonium zirconium carbonate, a zirconium (IV) butoxide, titanium chloride, or combinations thereof. The multivalent cation source compound may have an average particle size of from greater than or equal to about 1 nm to less than or equal to about 50 nm, from greater than or equal to about 1 nm to less than or equal to about 20 nm, or from greater than or equal to about 1 nm to less than or equal to about 10 nm. Without being bound to any theory, divalent cations are used in the multivalent cation source compound due to their relative size difference compared to the CNTs 8. Higher valency cations may be used in the multivalent cation source compound. However, their relative size difference compared to the CNTs 8 will be smaller, so the CNTs 8 may be more difficult to crosslink with higher valency cations.

In one embodiment, the CNTs 8 are functionalized with carboxylate groups 10 and the multivalent cation source compound is zinc oxide. During crosslinking, the zinc oxide reacts with the carboxylate groups 10 of the CNTs 8, crosslinking the CNTs as shown in FIG. 2 to form crosslinked CNTs 4'.

To form the crosslinked carbon nanostructures 4, such as the crosslinked CNTs 4', the carbon nanostructures and the cation source compound may be combined in solution with mixing (e.g., stirring). The carbon nanostructures and the multivalent cation source compound may be reacted in solution for a sufficient amount of time for the cation of the multivalent cation source compound to react with the functional groups of the carbon nanostructures. By way of example only, the carbon nanostructures and the multivalent cation source compound may be reacted for at least about 1 hour, such as for at least about 2 hours, at least about 3 hours, at least about 4 hours, at least about 5 hours, or greater. The carbon nanostructures and the multivalent cation source compound may be reacted with mixing at room temperature (e.g., between about 20° C. and about 25° C.). To increase the rate of reaction, the carbon nanostructures and the multivalent cation source compound may be combined with mixing at an elevated temperature, such as at a temperature of between about 30° C. and about 100° C. The temperature may be greater than about 30° C., greater than about 40° C., greater than about 50° C., greater than about 60° C., greater than about 70° C., greater than about 80° C., or greater than about 90° C. The carbon nanostructures and the multivalent cation source compound may be combined in an appropriate organic solvent (e.g., acetic acid, an anhydride of acetic acid, formic acid, an anhydride of formic acid, propionic acid, an anhydride of propionic acid, isobutyric acid, an anhydride of isobutyric acid), or combinations thereof. The carbon nanostructures may be present in the solution in excess compared to the multivalent cation source compound, such as at a weight ratio of greater than about 2:1 carbon nanostructures:multivalent cation source compound, greater than about 5:1 carbon nanostructures:multivalent cation source compound, or greater than about 10:1 carbon nanostructures:multivalent cation source compound.

As the carbon nanostructures and multivalent cation source compound react, the solution may change to a suspension. After the carbon nanostructures and the multivalent cation source compound have reacted for a sufficient amount of time to crosslink the carbon nanostructures, the crosslinked carbon nanostructures 4 may be recovered from the suspension. By way of example only, the crosslinked carbon nanostructures 4 may be filtered from the suspension and dried. By filtering the crosslinked carbon nanostructures 4, industrially viable amounts of the crosslinked carbon nanostructures 4 may be easily produced. The crosslinked carbon nanostructures 4 may then be disposed on or applied to the support substrate 6 to form the thin film substrate 2.

Figure 3A:
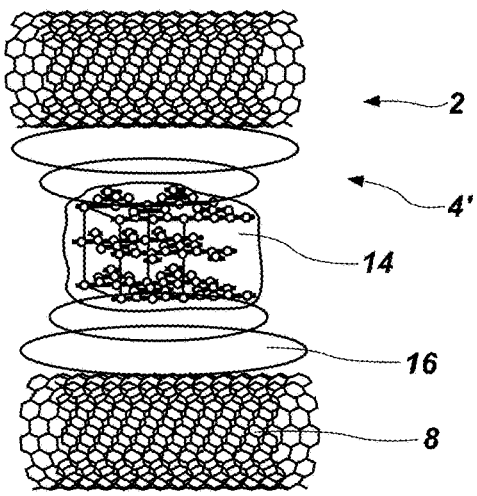
FIGS. 3a and 3b are schematic diagrams of thin film substrates including crosslinked carbon nanotubes according to another embodiment of the disclosure.
Figure 3B:
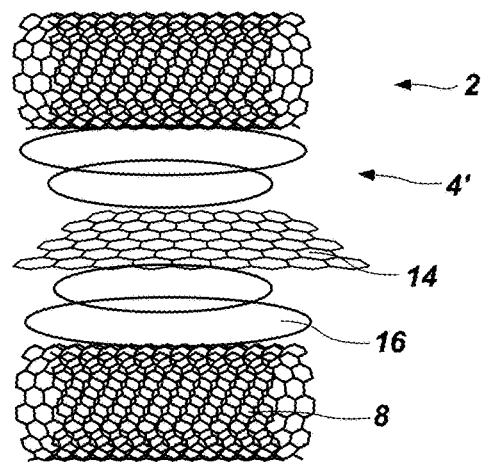

In another embodiment, the thin film substrate 2 includes CNTs 8 crosslinked by the pi-orbital source compound 14, as shown in FIGS. 3a and 3b. However, the thin film substrate 2 may, alternatively, include other carbon nanostructures crosslinked by the multivalent pi-orbital source compound 14. The CNTs 8 may be crosslinked by pi-pi stacking with the pi-orbital source compound 14. The pi-orbital source compound 14 may be any compound having pi-orbitals 16 including, but not limited, to graphene, carbon nitride ($CN_x$) where x is a positive real number, boron nitride (BN), $C_{60}$, a protein, or combinations thereof. The pi-orbital source compound 14 may have an average particle size of less than about 50 nm, less than about 20 nm, or less than about 10 nm. The average particle size of the pi-orbital source compound 14 may range from greater than or equal to about 1 nm to less than or equal to about 50 nm, from greater than or equal to about 1 nm to less than or equal to about 20 nm, or from greater than or equal to about 1 nm to less than or equal to about 10 nm. The pi-orbitals 16 of the pi-orbital source compound 14 overlap and stack with pi-orbitals 16 of the CNTs 8, crosslinking the CNTs 8 and forming the crosslinked CNTs 4'.

In one embodiment, the CNTs 8 are reacted with $CN_x$ (FIG. 3a) or graphene (FIG. 3b). The pi-orbitals 16 of the $CN_x$ or graphene react with the pi-orbitals 16 of the CNTs 8, crosslinking the CNTs as shown in FIGS. 3a and 3b.

To form the crosslinked carbon nanostructures 4, such as the crosslinked CNTs 4', the carbon nanostructures and the pi-orbital source compound may be combined in solution with mixing (e.g., stirring). The carbon nanostructures and the pi-orbital source compound may be reacted in solution for a sufficient amount of time for the pi-orbitals of the carbon nanostructures and the pi-orbitals of the pi-orbital source compound to overlap and stack. By way of example only, the carbon nanostructures and the pi-orbital source compound may be reacted for at least about 1 hour, such as for at least about 2 hours, at least about 3 hours, at least about 4 hours, at least about 5 hours, or greater. The carbon nanostructures and the pi-orbital source compound may be reacted with mixing at room temperature (e.g., between about 20° C. and about 25° C.). To increase the rate of reaction, the carbon nanostructures and the pi-orbital source compound may be combined with mixing at an elevated temperature, such as at a temperature of between about 30° C. and about 100° C. The temperature may be greater than about 30° C., greater than about 40° C., greater than about 50° C., greater than about 60° C., greater than about 70° C., greater than about 80° C., or greater than about 90° C. Sonication may, optionally, be used to sufficiently disperse the pi-orbital source compound and carbon nanostructures in the solution. The carbon nanostructures and the pi-orbital source compound may be combined in an appropriate solvent, such as water, an organic solvent, or combinations thereof. The carbon nanostructures may be present in the solution in excess compared to the pi-orbital source compound, such as at a weight ratio of greater than about 2:1 carbon nanostructures:pi-orbital source compound, greater than about 5:1 carbon nanostructures:pi-orbital source compound, or greater than about 10:1 carbon nanostructures:pi-orbital source compound.

As the carbon nanostructures and pi-orbital source compound react, the solution may change to a suspension. After the carbon nanostructures and the pi-orbital source compound have reacted for a sufficient amount of time to crosslink the carbon nanostructures, the crosslinked carbon nanostructures 4 may be recovered from the suspension. By way of example only, the crosslinked carbon nanostructures may be filtered from the suspension and dried. By filtering the crosslinked carbon nanostructures 4, industrially viable amounts of crosslinked carbon nanostructures 4 may be easily produced. The crosslinked carbon nanostructures may then be disposed on or applied to the support substrate 6 to form the thin film substrate 2.

Figure 4:
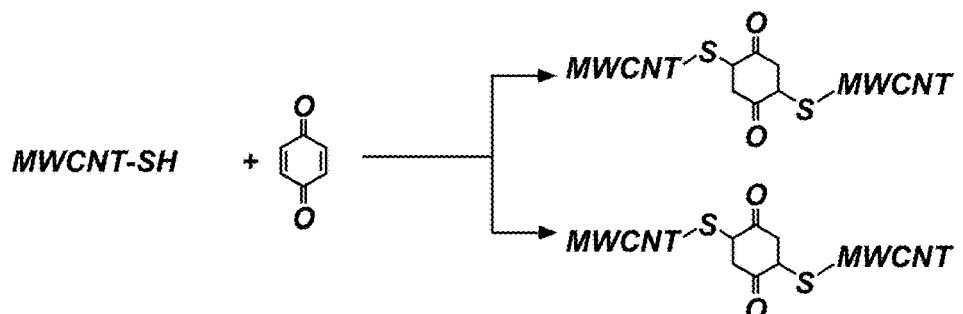
FIG. 4 is a schematic diagram of a thin film substrate including crosslinked carbon nanotubes according to yet another embodiment of the disclosure.

In yet another embodiment, the thin film substrate 2 includes CNTs 8, such as MWCNTs, crosslinked by covalent bonds formed between the CNTs 8 and the crosslinking agent, as shown in FIG. 4. However, the thin film substrate 2 may, alternatively, include other carbon nanostructures crosslinked by covalent bonds formed between the carbon nanostructures and the crosslinking agent. The CNTs 8 may be functionalized with a heteroatom-containing group, which reacts with and covalently bonds to the crosslinking agent. The thin film substrate 2 may be formed by crosslinking the CNTs 8 with the crosslinking agent. By way of example only, the heteroatom of the heteroatom-containing group may be sulfur or nitrogen, and reacts with the crosslinking agent. The crosslinking agent may include, but is not limited to, benzoquinone, an oligothiophene, an oligoaniline, phenylene sulfide, pyrrole, sulfur, a peroxide, urethane, a metallic oxide, boron oxide, acetoxysilane, an alkoxysilane, or combinations thereof. The crosslinking agent may have an average particle size of less than or equal to about 50 nm, less than or equal to about 20 nm, or less than or equal to about 10 nm, such as from greater than or equal to about 1 nm to less than or equal to about 50 nm, from greater than or equal to about 1 nm to less than or equal to about 20 nm, or from greater than or equal to about 1 nm to less than or equal to about 10 nm.

In one embodiment, the CNTs 8 are functionalized with a thiol group and the crosslinking agent is benzoquinone. During crosslinking, the sulfur atom of the functionalized CNTs reacts with the benzoquinone, crosslinking the CNTs as shown in FIG. 4.

To form the crosslinked carbon nanostructures 4, the carbon nanostructures and the crosslinking agent may be combined in solution with mixing (e.g., stirring). The carbon nanostructures and the crosslinking agent may be reacted in solution for a sufficient amount of time for the crosslinking agent to react with the functional group of the carbon nanostructures. By way of example only, the carbon nanostructures and the crosslinking agent may be reacted for at least about 1 hour, such as for at least about 2 hours, at least about 3 hours, at least about 4 hours, at least about 5 hours, or greater. The carbon nanostructures and the crosslinking agent may be reacted with mixing at room temperature (e.g., between about 20° C. and about 25° C.). To increase the rate of reaction, the carbon nanostructures and the crosslinking agent may be combined with mixing at an elevated temperature, such as at a temperature of between about 30° C. and about 100° C. The temperature may be greater than about 30° C., greater than about 40° C., greater than about 50° C., greater than about 60° C., greater than about 70° C., greater than about 80° C., or greater than about 90° C. Sonication may, optionally, be used to sufficiently disperse the crosslinking agent and carbon nanostructures in the solution. The carbon nanostructures and the crosslinking agent may be combined in an appropriate solvent, such as water, an organic solvent, or combinations thereof. The carbon nanostructures and crosslinking agent may be present in the solution in approximately stoichiometric amounts, such as between a weight ratio of 10:1 carbon nanostructures:crosslinking agent and 1:10 carbon nanostructures:crosslinking agent.

As the carbon nanostructures and crosslinking agent react, the solution may change to a suspension. After the carbon nanostructures and the crosslinking agent have reacted for a sufficient amount of time to crosslink the carbon nanostructures, the crosslinked carbon nanostructures 4 may be recovered from the suspension. By way of example only, the crosslinked carbon nanostructures 4 may be filtered from the suspension and dried. By filtering the crosslinked carbon nanostructure 4, industrially viable amounts of the crosslinked carbon nanostructures 4 may be easily produced. The crosslinked carbon nanostructures 4 may then be disposed on or applied to the support substrate 6 to form the thin film substrate 2. The reaction of the carbon nanostructures with the crosslinking agent produces crosslinked carbon nanostructures 4 having stronger crosslinking abilities than the pi-pi stacking embodiment described above and the electrostatic interactions embodiment described below. Thus, the resulting crosslinked carbon nanostructures 4' may be more durable than the crosslinked carbon nanostructures 4' produced by other techniques.

In addition to reaction with the crosslinking agent, covalently-bonded carbon nanostructures may be produced by crosslinking fluorine-functionalized carbon nanostructures or alkoxy-functionalized carbon nanostructures. If the carbon nanostructures are functionalized with fluorine groups, the carbon nanostructures may be crosslinked by reductive defluorination of the fluorine functionalized carbon nanostructures. The fluorinated carbon nanostructures may be exposed to UV irradiation, N,N,N'N'-tetramethyl-1,4,-benzenediamine, a diamine (e.g., ethylenediamine), or other reductive defluorination techniques to generate reactive free radicals on the defluorinated carbon nanostructures. A reductive defluorination agent, such as the diamine, may be present in excess compared to the carbon nanostructures, such as at a weight ratio of greater than about 2:1 reductive defluorination agent:carbon nanostructures, greater than about 5:1 reductive defluorination agent:carbon nanostructures, or greater than about 10:1 reductive defluorination agent:carbon nanostructures. The free radicals on the sidewalls of the carbon nanostructures may directly crosslink with one another under ambient conditions (ambient temperature and/or ambient pressure), forming the crosslinked carbon nanostructures 4'.

Figure 5:
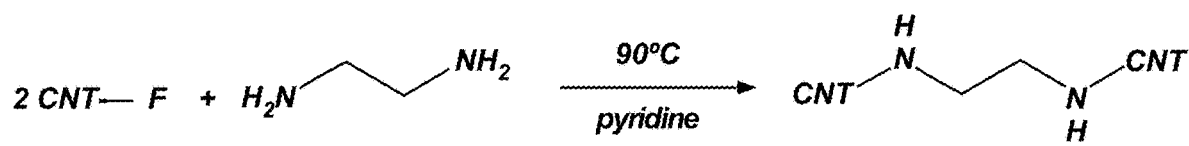
FIG. 5 is a schematic diagram of a thin film substrate including crosslinked carbon nanotubes according to yet another embodiment of the disclosure.

If the carbon nanostructures, such as CNTs 8, are functionalized with fluorine groups, the carbon nanostructures may be crosslinked using a diamine, such as ethylenediamine. In one embodiment, the CNTs 8 are functionalized with a fluorine group and the crosslinking agent is ethylenediamine. During crosslinking, nitrogen atoms of the ethylenediamine react with the fluorine-functionalized CNTs, crosslinking the CNTs 8 as shown in FIG. 5.

If the carbon nanostructures are functionalized with alkoxy groups, the carbon nanostructures may be crosslinked using peroxides or irradiation. The free radicals on the sidewalls of the carbon nanostructures may directly crosslink with one another under ambient conditions (temperature and/or pressure), forming the crosslinked carbon nanostructures 4. The fluorine-functionalized carbon nanostructures and alkoxy-functionalized carbon nanostructures may be crosslinked without using a crosslinking agent and without using high-temperature or high-pressure conditions.

Figure 6:
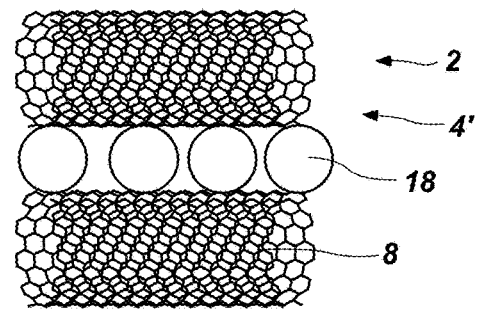
FIG. 6 is a schematic diagram of a thin film substrate including crosslinked carbon nanotubes according to an additional embodiment of the disclosure.

In yet another embodiment, the thin film substrate 2 includes CNTs 8 crosslinked by electrostatic interactions, as shown in FIG. 6. However, the thin film substrate 2 may, alternatively, include other carbon nanostructures crosslinked by the electrostatic interactions. Metal nanoparticles 18 may generate electrostatic interactions sufficient to hold together the CNTs 8. The metal nanoparticles 18 may include, but are not limited to, palladium, silver, gold, copper, platinum, ruthenium, rhodium, tin, aluminum, lithium, sodium, potassium, or combinations thereof. The metal nanoparticles 18 may have an average particle size of less than or equal to about 50 nm, less than or equal to about 20 nm, or less than or equal to about 10 nm, such as from greater than or equal to about 1 nm to less than or equal to about 50 nm, from greater than or equal to about 1 nm to less than or equal to about 20 nm, or from greater than or equal to about 1 nm to less than or equal to about 10 nm. Since the CNTs 8 are held together by electrostatic interactions, no crosslinking agent is utilized, increasing the cost-effectiveness and industrial viability of the crosslinked CNTs 4' crosslinked by electrostatic interactions.

In one embodiment, the CNTs 8 are crosslinked with palladium nanoparticles 18. During crosslinking, the palladium nanoparticles 18 interact with the CNTs 8, forming the crosslinked CNTs 4' as shown in FIG. 6.

To form the crosslinked carbon nanostructures 4, the carbon nanostructures and the metal nanoparticles 18 may be combined in solution with mixing (e.g., stirring). The carbon nanostructures and the metal nanoparticles 18 may be reacted in solution for a sufficient amount of time for the metal nanoparticles 18 and carbon nanostructures to interact.

By way of example only, the carbon nanostructures and the metal nanoparticles 18 may be combined in solution for at least about 1 hour, such as for at least about 2 hours, at least about 3 hours, at least about 4 hours, at least about 5 hours, or greater. The carbon nanostructures and the metal nanoparticles 18 may be combined at room temperature (e.g., between about 20° C. and about 25° C.). To increase the rate of reaction, the carbon nanostructures and the metal nanoparticles 18 may be combined with mixing at an elevated temperature, such as at a temperature of between about 30° C. and about 100° C. The temperature may be greater than about 30° C., greater than about 40° C., greater than about 50° C., greater than about 60° C., greater than about 70° C., greater than about 80° C., or greater than about 90° C. Sonication may, optionally, be used to sufficiently disperse metal nanoparticles 18 and carbon nanostructures in the solution. The carbon nanostructures and the metal nanoparticles 18 may be combined in an appropriate solvent, such as water, an organic solvent, or combinations thereof. The carbon nanostructures may be present in the solution in excess compared to the metal nanoparticles 18, such as at a weight ratio of greater than about 2:1 carbon nanostructures:metal nanoparticles, greater than about 5:1 carbon nanostructures:metal nanoparticles, or greater than about 10:1 carbon nanostructures:metal nanoparticles.

As the carbon nanostructures and metal nanoparticles 18 interact, the solution may change to a suspension. After the carbon nanostructures and the metal nanoparticles 18 have interacted for a sufficient amount of time to crosslink the carbon nanostructures, the crosslinked carbon nanostructures 4 may be recovered from the suspension. By way of example only, the crosslinked carbon nanostructures 4 may be filtered from the suspension and dried. By filtering the crosslinked carbon nanostructures 4, industrially viable amounts of the crosslinked carbon nanostructures 4 may be easily produced. The crosslinked carbon nanostructures 4 may then be disposed on (e.g., deposited on or applied to) the support substrate 6 to form the thin film substrate 2.

The thin film substrates 2 of the disclosure, which include the crosslinked carbon nanostructures 4 on the support substrate 6, may exhibit an increased resistance to swelling when liquid samples are analyzed by SERS using the thin film substrates 2. The crosslinked carbon nanostructures 4 may prevent swelling of the thin film substrates 2 of the disclosure when liquid samples are analyzed. By crosslinking the carbon nanostructures, stronger bonds or stronger interactions are formed between the carbon nanostructures, improving mechanical properties of the thin film substrates 2. In contrast, thin film substrates 2 formed from conventional techniques, such as by mechanical compression or laser ablation, rely on van der Waals interactions to keep the carbon nanostructures together. These conventional thin film substrates swell and deteriorate when used to analyze liquid samples by SERS. Additionally, since the thin film substrates 2 of the disclosure include crosslinked carbon nanostructures 4, pore sizes of the thin film substrates 2 are decreased. Therefore, liquid samples to be analyzed by SERS can be uniformly placed on a surface of the thin film substrates 2 of the disclosure. The thin film substrates 2 of the disclosure may also exhibit an increased resistance to swelling when used in filtration or chemical sensing applications.

The methods of forming the thin film substrates 2 of the disclosure may be readily scaled up for industrial production of the thin film substrates 2 since the thin film substrates 2 are produced by filtration-from-suspension techniques. Therefore, the need for specialized and costly equipment, such as high energy lasers or high pressure/high temperature reaction chambers, is reduced or eliminated.

To further increase the sensitivity of the thin film substrates 2, metallic nanowires may optionally be present in the thin film substrates 2 of the disclosure. By way of example only, nanowires formed of platinum, copper, silver, gold, ruthenium, rhodium, tin, palladium, aluminum, lithium, sodium, potassium, or combinations thereof may, optionally, be present in the thin film substrates to synergistically increase detection of the SERS-active analyte. The nanowires are formed by conventional techniques. Since the thin film substrates 2 that are crosslinked using the metal nanoparticles already include a conductive material, these thin film substrates 2 exhibit increased sensitivity in SERS detection without including the optional nanowires.

Liquid samples including a SERS-active analyte may be analyzed by SERS using the thin film substrates 2 according to embodiment of the disclosure. The SERS-active analyte may be placed on the thin film substrate 2 and the thin film substrate 2 exposed to Raman scattering to detect the SERS-active analyte. The thin film substrate 2 may include or may lack the support substrate 6. Thus, methods of performing SERS using the thin film substrate are also disclosed.

The thin film substrates 2 according to embodiments of the disclosure may also be used as a membrane to filter a liquid sample or a gaseous sample. The thin film substrate 2 may exhibit a high surface area and porosity, enabling the thin film substrate 2 to be used to purify or otherwise remove contaminants or other undesired components of the sample. The crosslinked carbon nanostructures 4 of the thin film substrate 2 may exhibit chemical resistance to and chemical compatibility with components of the liquid sample. The crosslinked carbon nanostructures 4 of the thin film substrate 2 may also exhibit antifouling properties. The thin film substrate 2 may include or may lack the support substrate 6 as long as the thin film substrate 2 exhibits sufficient porosity for the sample to flow through the membrane. By way of example only, the thin film substrate 2 may be used to filter water.

The thin film substrates 2 according to embodiments of the disclosure may also be used in a chemical sensor to detect an analyte (e.g., a chemical species) in a liquid sample or in a gaseous sample. The chemical species may include, but is not limited to, a chemical composition, a chemical compound, an element, or an ion. The thin film substrate 2 may include a chemical recognition structure on a portion of a surface of the thin film substrate 2, which reacts with the analyte to detect the chemical species in the sample. The thin film substrate 2 may include or may lack the support substrate 6. By way of example only, the thin film substrate 2 may be used to detect hydrogen ($H_2$) gas in a gaseous sample, such as by using palladium to detect the $H_2$. The thin film substrate 2 may also be used to detect mercury (Hg) in a liquid sample, such as by using gold to detect the $H_2$.

Example 1

Fluorinated CNT Crosslinking with Ethylenediamine

Figure 7:
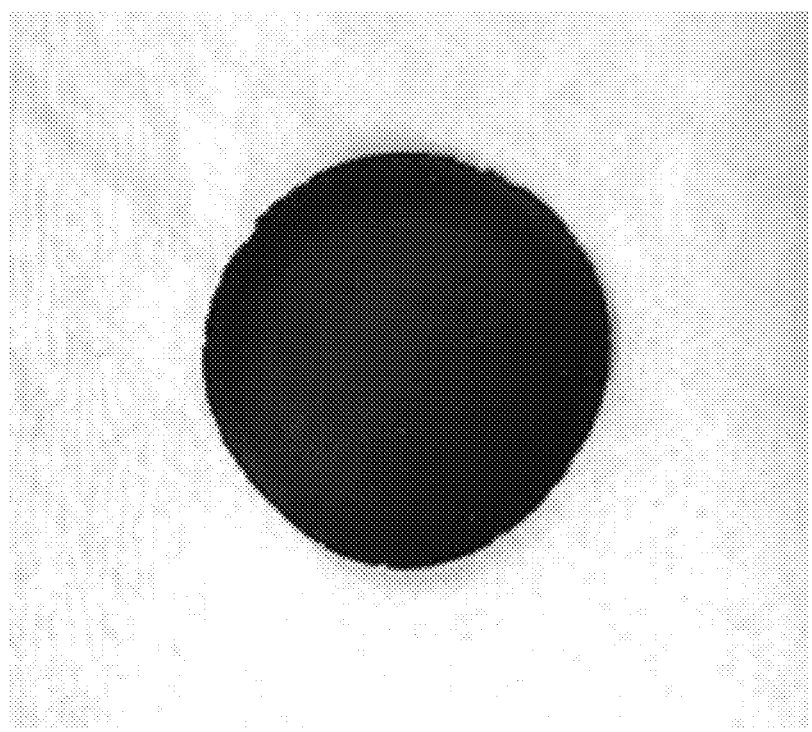
FIG. 7 is a photograph of crosslinked carbon nanotubes according to an additional embodiment of the disclosure.
Figure 8:
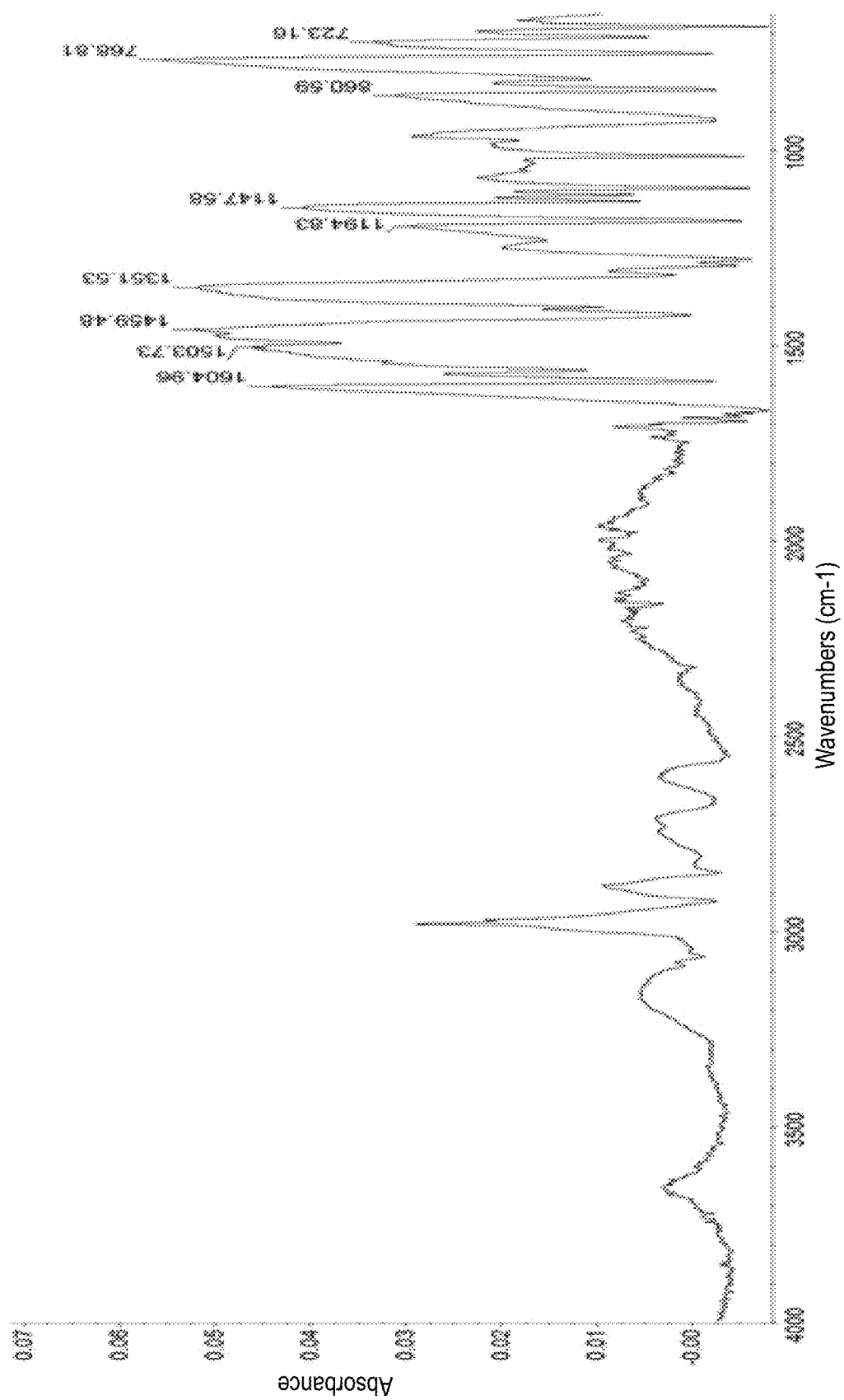
FIG. 8 is a fourier transform infrared (FTIR) spectrum of the crosslinked carbon nanotubes shown in FIG. 7.

A 5:1 ratio by weight of ethylenediamine and fluorinated carbon nanotubes (CNT-F), respectively, were dispersed in orthodichlorobenzene to form a mixture. Five drops of pyridine was also added to scavenge and neutralize HF byproducts. The mixture was stirred for 3 hours at 90° C. under an inert atmosphere to crosslink the CNT-F, as confirmed by FTIR. To recover the crosslinked CNTs, the mixture was filtered by vacuum filtration (by filtration-fromsuspension techniques) on filter paper, producing a mat of the crosslinked CNTs as shown in FIG. 7. As shown in FIG. 8, unreacted fluorine groups of the CNT-F (as evidenced by a peak at 1147 cm$^{-1}$) of the FTIR spectrum) may provide hydrophobic properties.

Embodiment 1: A method of making a thin film substrate, comprising: exposing carbon nanostructures to a crosslinker to crosslink the carbon nanostructures; recovering the crosslinked carbon nanostructures; and disposing the crosslinked carbon nanostructures on a support substrate.

Embodiment 2: The method of Embodiment 1, wherein exposing carbon nanostructures to a crosslinker comprises exposing functionalized carbon nanostructures to the crosslinker.

Embodiment 3: The method of Embodiment 1, wherein exposing carbon nanostructures to a crosslinker comprises exposing carbon nanotubes or graphene to the crosslinker.

Embodiment 4: The method of Embodiment 1, wherein exposing carbon nanostructures to a crosslinker comprises exposing carbon nanostructures functionalized with carboxylate groups, fluorine groups, amino groups, hydroxyl groups, or thiol groups to the crosslinker.

Embodiment 5: The method of Embodiment 1, wherein exposing carbon nanostructures to a crosslinker comprises exposing the carbon nanostructures to a multivalent cation source compound comprising a divalent metal oxide, a divalent metal alkoxide, a salt or complex of the divalent cation, or combinations thereof.

Embodiment 6: The method of Embodiment 1, wherein exposing carbon nanostructures to a crosslinker comprises exposing the carbon nanostructures to a pi-orbital source compound comprising graphene, carbon nitride, boron nitride, or combinations thereof.

Embodiment 7: The method of Embodiment 1, wherein exposing carbon nanostructures to a crosslinker comprises exposing the carbon nanostructures to a crosslinking agent comprising benzoquinone, an oligothiophene, an oligoaniline, phenylene sulfide, pyrrole, sulfur, a peroxide, urethane, a metallic oxide, boron oxide, acetoxysilane, an alkoxysilane, or combinations thereof.

Embodiment 8: The method of Embodiment 1, wherein exposing carbon nanostructures to a crosslinking agent comprises exposing the carbon nanostructures to metal nanoparticles comprising nanoparticles of palladium, silver, gold, copper, platinum, ruthenium, rhodium, tin, aluminum, lithium, sodium, potassium, or combinations thereof.

Embodiment 9: The method of Embodiment 1, wherein exposing carbon nanostructures to a crosslinker to crosslink the carbon nanostructures comprises exposing the carbon nanostructures to the crosslinker at ambient conditions.

Embodiment 10: The method of Embodiment 1, wherein exposing carbon nanostructures to a crosslinker to crosslink the carbon nanostructures comprises crosslinking the carbon nanostructures in solution.

Embodiment 11: The method of Embodiment 1, wherein recovering the crosslinked carbon nanostructures comprises filtering the crosslinked carbon nanostructures from a suspension comprising the crosslinked carbon nanostructures.

Embodiment 12: A thin film substrate comprising crosslinked carbon nanostructures on a support substrate, the crosslinked carbon nanostructures comprising a crosslinker between the carbon nanostructures.

Embodiment 13: The thin film substrate of Embodiment 12, wherein the crosslinker comprises a multivalent cation, a pi-orbital source compound, a crosslinking agent, or metal nanoparticles.

Embodiment 14: The thin film substrate of Embodiment 12, wherein the crosslinker comprises a divalent cation.

Embodiment 15: The thin film substrate of Embodiment 12, wherein the crosslinker comprises graphene or carbon nitride.

Embodiment 16: The thin film substrate of Embodiment 12, wherein the crosslinker comprises benzoquinone.

Embodiment 17: The thin film substrate of Embodiment 12, wherein the crosslinker comprises palladium nanoparticles, copper nanoparticles, silver nanoparticles, gold nanoparticles, or combinations thereof.

Embodiment 18: The thin film substrate of Embodiment 12, wherein the crosslinked carbon nanostructures comprise crosslinked carbon nanotubes or crosslinked graphene.

Embodiment 19: A method of performing surface enhanced Raman spectroscopy (SERS) to detect a SERS-active analyte comprising providing a SERS-active analyte on a thin film substrate, exposing the thin film substrate to Raman scattering, and detecting the SERS-active analyte. The thin film substrate comprises crosslinked carbon nanotubes on a support substrate and the crosslinked carbon nanotubes comprise a crosslinker between the carbon nanotubes.

While the disclosure is susceptible to various modifications and alternative forms, specific embodiments have been shown by way of example in the drawings and have been described in detail herein. However, the disclosure is not intended to be limited to the particular forms disclosed. Rather, the disclosure is to cover all modifications, equivalents, and alternatives falling within the scope of the disclosure as defined by the following appended claims and their legal equivalents.

What is claimed is:

1. A method of making a thin film substrate, comprising:
forming a solution of carbon nanostructures;
reacting the carbon nanostructures with a crosslinker to form a suspension comprising
crosslinked carbon nanostructures comprising covalent bonds between the crosslinked carbon nanostructures and the crosslinker, the crosslinker comprising a multivalent cation source compound comprising an oligothiophene, an oligoaniline, phenylene sulfide, pyrrole, urethane, a metallic oxide, boron oxide, acetoxysilane, or a combination thereof;
filtering the crosslinked carbon nanostructures from the suspension; and
disposing the crosslinked carbon nanostructures on a support substrate.

2. The method of claim 1, wherein reacting the carbon nanostructures with a crosslinker comprises exposing functionalized carbon nanostructures to the crosslinker.

3. The method of claim 1, wherein reacting the carbon nanostructures with a crosslinker comprises exposing carbon nanotubes or graphene to the crosslinker.

4. The method of claim 1, wherein reacting the carbon nanostructures with a crosslinker comprises crosslinking the carbon nanostructures in solution.

\* \* \* \* \*